US006689718B2

United States Patent

(12) United States Patent
Charudattan et al.

(10) Patent No.: US 6,689,718 B2
(45) Date of Patent: Feb. 10, 2004

(54) USE OF TOBACCO MILD GREEN MOSAIC VIRUS (TMGMV) MEDIATED LETHAL HYPERSENSITIVE RESPONSE (HR) AS A NOVEL METHOD OF WEED CONTROL

(75) Inventors: Raghavan Charudattan, Gainesville, FL (US); Matthew Scott Pettersen, Gainesville, FL (US); Ernest Hiebert, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 11 days.

(21) Appl. No.: 09/997,054

(22) Filed: Nov. 29, 2001

(65) Prior Publication Data

US 2003/0125208 A1 Jul. 3, 2003

(51) Int. Cl.[7] .................... A01N 63/00
(52) U.S. Cl. .................... 504/117
(58) Field of Search .................... 504/117

(56) References Cited

U.S. PATENT DOCUMENTS 4,162,912 A 7/1979 Charudattan

OTHER PUBLICATIONS

Pettersen, M. et al., Tobacco mild green mosaic tobamovirus strain U2 causes a lethal hypersensitive response in Salanum viarum Dual (tropical soda apple) Abstr. Meet. Weed Sci. Soc. AM 40;84, 2000.

Pettersen, M. Tobacco mild green mosalc virus (TMGMV) induces a lethal hypersensitive response in tropical soda apple (Solanum viarum Dunal), Phytopahtology, 91(6):S71–S72., 2001 (abstract).

Students of the Plant Pathology Dept, The Newsletter of the Plant Pathology Dept. at the University of Florida, 5(1), page 3 column 2, paragraph 1, 2001.

Students of the Plant Pathology Dept, The Newsletter of the Plant Pathology Dept. at the University of Florida, 5(2), page 3 column 2, paragraphs 2–3, 2001.

Session and Oral Presentations, Aps. Son. MSA Joint Meeting, Aug. 25–29, 2001.

Akanda, R.U., Dowler, C.C., Mullahey, J.J., and Shilling, D.G. 1997. Influence of postemergence herbicides on tropical soda apple (*Solanum viarum*) and Bahiagrass (*Paspalum notatum*). Weed Technol. 11:656–661.

Chisholm, S.T., Mahajan, S. J., Whitham, S. A., Yamamoto, M. L. and Carrington, J. C. 2000. Cloning of the Arabidopsis RTM1 gene, which controls restriction of long–distance movement of tobacco etch virus. Proc. Natl. Acad. Sci. 97:489–494.

Culver, J.N. 1997. Viral avirulence genes. Chapter 6. Pages 196–219 in: G. Stacey and N.T. Keen, eds. Plant–Microbe Interactions, vol. 2. Chapman & Hall, New York.

Culver , J. N., and Dawson, W. O. 1991. Tobacco mosaic virus elicitor coat protein genes produce a hypersensitive phenotype in transgenic Nicotiana sylvestris plants. Mol. Plant–Microbe Interact. 4:458–463.

Dawson, W.O. 1999. Tobacco mosaic virus virulence and avirulence. Phil. Trans. R. Soc. Lond. B 354:643–651.

Duan, Y.P., Castañeda, A., Zhao, G., Erdos, G., Gabriel, D.W. 1999. Expression of a single, host specific, bacterial pathogenicity gene in plant cells elicits division, enlargement, and cell death. Molec. Plant–Microbe Interact. 12:556–560.

Erickson, F. L., Holzberg, S., Calderon–Urrea, A., Handley, V., Axtell, M., Corr, C., and Baker, B. 1999. The helicase domain of the TMV replicase proteins induces the N–mediated defense response in tobacco. Plant Journal 18, 67–75.

McGovern, R.J., Polston, J.E., and Mullahey, J.J. 1994. *Solanum viarum* Dunal: weed reservoir of plant viruses in Florida. Int. J. Pest Manage. 40:270–273.

Mullahey J.J. 1996. Tropical soda apple (*Solanum viarum* Dunal), a biological pollutant threatening Florida. Castanea 61:255–260.

Padgett, H. S. Watanabe, Y., and Beachy, R. N. 1997. Identification of the TMV replicase sequence that activates the N gene–mediated hypersensitive response. Mol. Plant–Microbe Interact. 10:709–715.

Purcifull, D.E. 1990. Ouchterlony double–diffusion tests in the presence of sodium dodecyl sulfate for detection of virion proteins and virus–induced inclusion proteins. pp. 179–196 in: R. Hampton, E. Ball, and S. De Boer, eds., Serological Methods for the Detection and Identification of Viral and Bacterial Plant Pathogens, APS Press, St. Paul, MN.

Saito, T., Meshi, T., Takamatsu, N., and Okado, Y. 1987. Coat protein gene sequences of tobacco mosaic virus encodes host response determinant. Proc. Natl. Acad. Sci. USA 84:6074–6077.

Shivprasad, S., Pogue, G.P., Lewandowski, J., Hidalgo, J., Donson, J., Grill, L.K., and Dawson, W.O. 1999. Heterologous sequences greatly affect foreign gene expression in tobacco mosaic virus–based vectors. Virology 255:312–323.

Weber, H. and Pfitzner, J.P. 1998. T*m*–$2^2$ resistance in tomato requires recognition of the carboxy terminus of the movement protein of tomato mosaic virus. Molec. Plant–Microbe Interact. 11:498–503.

*Primary Examiner*—Alton Pryor
(74) *Attorney, Agent, or Firm*—Saliwanchik, Lloyd & Saliwanchik

(57) ABSTRACT

Tobacco mild green mosaic virus (TMGMV) induces a lethal, systemic, hypersensitive response in Tropical Soda Apple (TSA). TMGMV is a member of the tobamoviruses, which consist of mechanically transmitted, rod-shaped, RNA viruses that are strictly plant pathogens.

10 Claims, 3 Drawing Sheets

(3 of 3 Drawing Sheet(s) Filed in Color)

USE OF TOBACCO MILD GREEN MOSAIC VIRUS (TMGMV) MEDIATED LETHAL HYPERSENSITIVE RESPONSE (HR) AS A NOVEL METHOD OF WEED CONTROL

FIELD OF THE INVENTION

The subject invention pertains to the field of agriculture, more particularly to the biocontrol of undesirable plant species.

BACKGROUND OF THE INVENTION

Tropical soda apple (*Solanum viarum* Dunal; TSA) is a prickly perennial weed species indigenous to South America. Introduced into Florida in 1988 it has since become one of the most serious invasive weeds in the southeastern United States (Mullahey, 1996). Tropical soda apple is designated a noxious weed under the Federal Noxious Weed Statutes. It proliferates rapidly by both sexual and asexual means. TSA is dispersed by cattle, birds, wild animals, and certain ranching and agricultural practices. In addition to being a highly competitive weed, TSA poses an additional threat as a reservoir for several economically important plant viruses (McGovern et al., 1994). TSA is currently managed by a combination of mowing and application of the chemical herbicide triclopyr (Remedy®) (Akanda et al., 1997), but alternative means of control are necessary and desirable.

SUMMARY OF THE INVENTION

All references cited herein are incorporated by reference in their entirety, to the extent not inconsistent with the explicit teachings set forth herein.

As an alternative to chemical herbicides, we searched for a suitable pathogen of tropical soda apple (TSA) for development as a bioherbicide and have discovered that Tobacco mild green mosaic virus (TMGMV) induces a lethal, systemic, hypersensitive response in TSA. TMGMV is a member of the tobamoviruses, which consist of mechanically transmitted, rod-shaped, RNA viruses that are strictly plant pathogens. The type species of Tobamovirus is Tobacco mosaic virus U1 (TMV U1), a widely distributed plant virus. Unlike TMGMV, TMV U1 and Tomato mosaic virus (ToMV, another Tobamovirus species), caused only mild, nonlethal mosaic or mottling of the TSA leaves. The atypical lethal effect of TMGMV on TSA was unexpected and is previously unknown. Also unknown was the feasibility to use TMGMV as a biocontrol for TSA.

Tropical soda apple serves as a host for TMV U1, ToMV, and TMGMV. In contrast to the mild, systemic mosaic symptoms caused by TMV U1 and ToMV, TMGMV causes rapid death of TSA. This death occurs due to a massive, systemic, hypersensitive plant response to infection by the virus. Both serological and molecular evidence confirm that TMGMV is responsible for the rapid and high rate of mortality on TSA. The age of TSA at the time of TMGMV inoculation does not affect the mortality rates, but the first expression of symptoms and first plant mortality are slightly delayed in older plants as compared to younger plants. Thus, the ability to control TSA by TMGMV is not limited by plant age. Temperature is usually not a limiting factor, although disease development will be slowed or prevented if the inoculated TSA plants are maintained continuously at 32° C. (or presumably at higher temperatures). However, under normal field conditions, a diurnal temperature fluctuation will occur and as our results indicate, TMGMV kills TSA plants under the diurnal cycle of 32/22° C. temperatures. To avoid possible adverse effects of high temperatures according to the subject invention, the TMGMV is preferably used in the field during the cooler months of spring and fall.

The host reaction of two *C. annuum* cultivars indicates that, as a precaution, TMGMV should not be used in the vicinity of pepper crops. However, it is safe to use the virus near tomato and eggplant crops.

Field trials from Hawthorne (north-central Florida) and Deseret Ranch (south-central Florida) sites confirm the excellent efficacy of TMGMV as a biological control agent for TSA. The high temperature-induced, attenuated disease symptoms, seen in plants incubated at 32° C., did not occur at either field site. Furthermore, the levels of TSA control obtained with TMGMV were comparable to the control levels obtained with chemical herbicides, but without the risks of chemical contamination.

Other advantages of TMGMV are first, the feasibility to produce abundant supplies of the virus by a simple, inexpensive method in susceptible tobacco; and second, the extremely small doses needed for high levels of TSA control. This virus-based bioherbicide system can be produced, developed, and registered more easily than fungal-based bioherbicides. Another important aspect of the TSA-TMGMV system is its highly novel mode of action, which is based on a systemic hypersensitive host response triggered by a gene of the virus.

Accordingly, it is an object of the present invention to provide a novel method of weed control.

It is a further object of the present invention to provide a method of weed control utilizing tobomoviruses.

It is a still further object of the present invention to provide a method of weed control utilizing TMGMV.

It is a still further object of the present invention to provide a method of controlling the tropical soda apple utilizing TMGMV.

Further objects and advantages of the present invention will become apparent by reference to the following detailed disclosure of the invention and appended photographs.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
FIG. 1 is a photograph depicting the mosaic symptoms caused by TMV U1.
Figure 2:
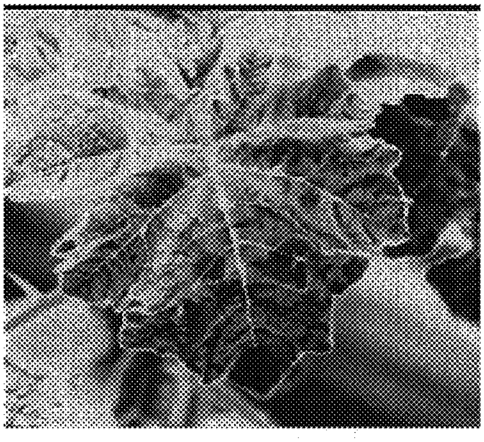
FIG. 2 is a photograph depicting the mosaic symptoms caused by ToMV.
Figure 3:
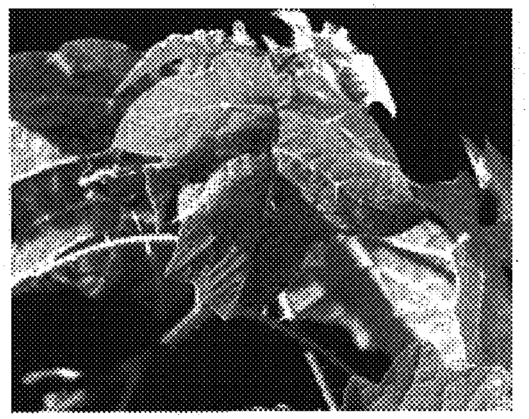
FIG. 3 is a photograph depicting the mosaic symptoms caused by TMGMV.

Following are examples which illustrate procedures for practicing the invention. These examples should not be construed as limiting. All percentages are by weight or numbers and all solvent mixture proportions are by volume unless otherwise noted.

EXAMPLE 1

Virus Isolates

Three tobamovirus isolates, Tobacco mild green mosaic virus (TMGMV), Tobacco mosaic virus (TMV U1), and Tomato mosaic virus (ToMV) are used. These viruses are maintained in infected, frozen, tobacco tissue in the plant virus collection at the Plant Pathology Department, University of Florida, Gainesville.

Plant Materials

*Nicotiana tabacum* L. cultivar Turkish Samsun nn (tobacco) is used as the susceptible host to maintain the tobamovirus species and produce their inocula. Tobacco (*Nicotiana tabacum* L.) cv. Turkish Samsun NN, a TMV-resistant variety, which develops hypersensitive local lesions on leaves, in response to infection by these tobamoviruses, is used to assay the viruses for efficacy of their inocula. The TSA seeds used in this study are collected from TSA-infested infested sites in southern Florida, primarily in Immokalee, Fla.

The tobacco and TSA seeds are sown at a depth of about 3–4 mm in seedling trays containing Metro-Mix® 300 potting soil (Scotts-Sierra Horticultural Products Company, Marysville, Ohio). At 1- to 2-leaf stage, the seedlings are transplanted singly into individual 6-cm-diameter pots. The plants are grown under natural sunlight in a greenhouse. To reduce the risk of cross contamination, the tobacco and TSA plants inoculated with each tobamovirus species are maintained in separate greenhouses.

Pathogenicity Testing of TMV U1, ToMV, and TMGMV on TSA

The susceptibility of TSA to TMV U1, ToMV, and TMGMV is determined in comparison with the reaction of susceptible and resistant tobacco to these viruses. Five susceptible (nn) and two resistant (NN) tobacco plants are manually inoculated with inoculum prepared by triturating about 20 mg of each frozen tobamovirus sample in 0.02 M sodium phosphate buffer (pH 7.2). The susceptible tobacco plant also serves as the inoculum source for all subsequent experiments. About 20 mg of carborundum (320 grit) is added to the buffer-virus preparation to serve as an abrasive. The TSA plants (approx. 60-day-old) are inoculated by gently rubbing the leaf on the abaxial midrib from leaf tip to leaf base with a piece of cheesecloth soaked in inoculum. The prickles on the midrib typically snap easily in this direction. The control TSA plants are treated similarly but with buffer+carborundum only. The trial is performed two times, each with 10 plants for the inoculated treatment and two plants for the control.

Referring now to FIGS. 1–4, all three tobamoviruses infect TSA. In resistant Turkish Samsun NN plants inoculated with the tobamoviruses, hypersensitive local lesions develop in the leaves in 3 to 4 days. In comparison, the susceptible nn tobacco develop mild, systemic mosaic symptoms at 9, 14, and 10 days after inoculation with TMV U1 (FIG. 1), ToMV (FIG. 2), and TMGMV (FIG. 3), respectively. The first symptom expression in TSA inoculated with TMGMV appears in 6–8 days, compared with an average of 13 and 16 days for TMV U1 and ToMV. TMVU1 and ToMV cause the same systemic mosaic symptoms in leaves of inoculated TSA plants in both trials.

Figure 4:
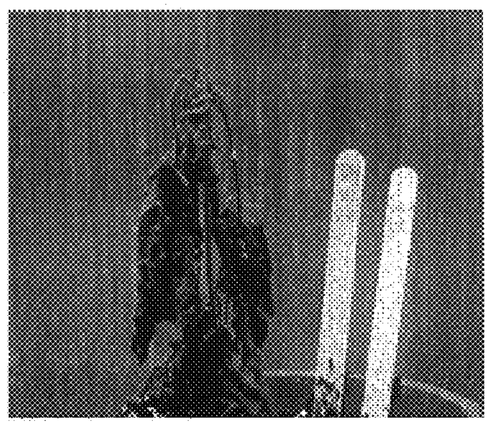
FIG. 4 is a photograph depicting the lethal systemic necrosis caused by TMGMV, two weeks post-inoculation.
Figure 5:
FIG. 5 is a photograph depicting the effect of TMGMV on 2-month-old TSA, 1–2 weeks post inoculation.
Figure 6:
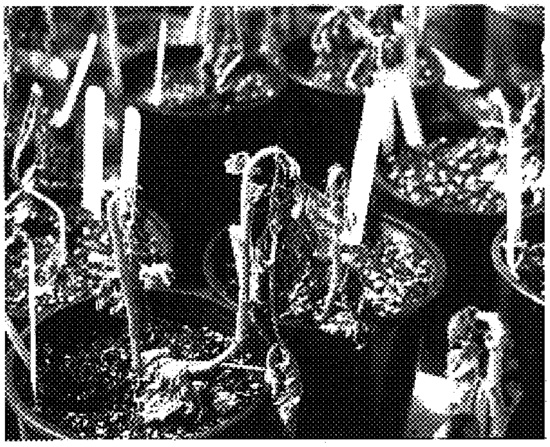
FIG. 6 is a photograph depicting the effect of TMGMV on 3-month-old TSA, 2 weeks post inoculation.
Figure 7:
FIG. 7 is a photograph depicting the effect of TMGMV on 7-month-old TSA, approximately one-month post inoculation.

Compared with TMV U1 and ToMV, TMGMV produces a devastating systemic necrosis (FIG. 4). In two trials, 100% of the inoculated TSA plants are killed by a systemic hypersensitive response (HR). Mock-inoculated control TSA plants remain healthy. Leaf drop and dieback occurs 5 to 6 days after the onset of first symptoms. After 6 days, severe wilting occurs with dark-gray to black necrotic lesions on inoculated leaves. The wilted plants are kept watered to determine whether the plants would regenerate by producing suckers. Three of the TSA plants that die down to the soil level produce suckers and regenerate. Initially, the new suckers are asymptomatic, but after a few weeks, these seemingly healthy suckers die from systemic HR.

SDS Immunodiffusion Tests

The presence or absence of the viruses in plant tissues and their identities are confirmed with the aid of immunodiffusion tests. These tests are done as follows: At approximately 1–3 weeks after inoculation, newly developed leaves from virus-inoculated and control TSA plants are collected, and their saps extracted with the aid of a mechanical sap extractor. The saps are diluted 1:1 in sterile water and then further diluted to 1:1:1 volume with 3% sodium dodecyl sulfate (SDS) prior to loading in immunodiffusion plates. The immunodiffusion tests are done as described by Purcifull (1990) using 0.8% Noble agar, 0.5% SDS and 1.0% $NaN_3$. TMV U1, ToMV, and TMGMV antisera are obtained from the collection of antisera available at the Plant Pathology Department, University of Florida.

In immunodiffusion tests, the TMGMV antiserum produces identical precipitin bands with antigens from the TMGMV-inoculated Turkish Samsun nn tobacco (TMGMV-Tobacco) and TSA (TMGMV-TSA), confirming that the same virus is present and responsible for the observed symptoms in both plants. The TMGMV antiserum does not react with antigens prepared from healthy TSA plants. The TMV U1 antiserum produces precipitin lines with antigens from TMV U1-inoculated Turkish Samsun nn tobacco (TMV U1-Tobacco) and TMGMV-inoculated TSA (TMGMV-TSA) plants. The precipitin bands spur over, indicating partial identity of the two antigens. Likewise, ToMV-TSA and TMGMV-TSA antigens show partial identity against ToMV antiserum. The ToMV antiserum reacts with ToMV-inoculated Turkish Samsun nn tobacco (ToMV-Tobacco) and TSA (ToMV-TSA) and produces precipitin bands that spur over in reactions with ToMV-TSA and TMV U1-TSA antigens. The preimmune blank antisera do not react with antigens from tobacco or TSA infected with any of the tobamoviruses.

Experimental Culture of TMGMV vs. a cDNA Clone

The TMGMV isolate used in this study is compared against a cDNA-derived clone of TMGMV (cDNA clone) to confirm that our isolate consists of a pure culture. The cDNA clone is provided by W. O. Dawson, Citrus Research and Education Center, IFAS, University of Florida, Lake Alfred. Inocula of our TMGMV isolate and the cDNA clone are produced in Turkish Samsun nn tobacco. Each virus inoculum is manually inoculated on five TSA and three Turkish Samsun NN tobacco plants. The plants are 45- to 60-day old transplants at the time of inoculation. This experiment is done twice to confirm the results.

Both cDNA clone and the test isolate of TMGMV multiplied in Turkish Samsun nn tobacco and inoculated into TSA produce initial symptoms on TSA at 6 days after inoculation. All plants in trial 1 inoculated with the test TMGMV isolate or the cDNA clone die by 10 days after inoculation. In Trial 2, the TMGMV test isolate completely kills TSA plants by 10 days, whereas the cDNA clone kills two plants by the 10th day. The remaining three TSA plants inoculated with the cDNA clone have systemic necrosis, and newly emergent leaves develop mosaic and necrotic flecks. These plants are severely stunted and lignified throughout the main stems and branches.

Effect of Plant Age on TMGMV Disease Development

The effect of TSA plant age on the susceptibility of this plant to TMGMV is tested. This experiment is done twice with six age categories of greenhouse-grown TSA plants: less than 1-month, 1-month, 2-months, 3-months, 7-months, or more than 1-year old. Plants for the age-effect experiment are grown in Metro-Mix® 300 potting medium amended with Multicote®(15-15-15:N-P-K, TRI-Pro Inc., Apopka, Fla.). TSA seed is sown on a monthly basis prior to the experiment, except for the more-than-1-year category. Plants for this category come from those that have been previously maintained in a greenhouse. There are 6 to 10 plants for inoculated treatments and 2 for controls. Plants of all age categories are inoculated manually, as described above, with the TMGMV inoculum produced in Turkish Samsun nn tobacco.

The plants are monitored for symptom development over time. Plant death is defined as the complete defoliation and severe necrosis of aboveground parts. The time of appearance (in days) of the first symptoms and time of first death are recorded for each age group. The data are analyzed using SAS (Statistical Analysis Systems, Cary, N.C.) by analysis of variance. Significant means are separated by Duncan's multiple range test.

Figure 8:
FIG. 8 is a photograph depicting mock inoculated (buffer only) control plants, 2 weeks post inoculation.

Referring now to FIGS. 5–8, the age of the TSA plant influences the speed of symptom development (i.e., day when first symptom development appears) as well as plant mortality (i.e., day when the first plant death is noted). (Table 1). The first symptoms are foliar local lesions. This is followed by severe wilting and necrosis on the stems and petioles, and complete collapse of the leaf tissues. Within one month after inoculation, 100% of the inoculated TSA plants die in both trials. Symptoms appear sooner in plants less than 3-months-old (FIGS. 5 and 6) compared to 7-months-old (FIG. 7) or older-than-1-year plants. (Table 2). In trial 1, older-than-1-year plants develop symptoms later than 7-month-old plants. In trial 2, this order is reversed. TSA plants less than 1-month-old and 3-month-old are killed most quickly compared with older plants, which took twice as long to die. Suckers emerge from three treated plants: a healthy sucker emerges in the first trial from a 3-month-old plant. This sucker grows for about 2 to 3 months and then dies from systemic HR. A second sucker then emerges from the same plant, grows for about 5 months, and then dies from systemic HR. No further suckers emerge from this plant, indicating total kill. The two remaining plants that sucker are the 1-month and 7-months old. These suckers are severely stunted (max. height of ca. 10–15 cm) and leaves on these suckers have necrotic lesions. Three months later, leaves from each of these mosaic-displaying suckers are individually triturated and the sap inoculated into three healthy 4- to 5-month-old TSA plants. About one week after inoculation, the plants develop systemic necrosis accompanied by leaf abscission. In the following 3 weeks, newly emerged leaves produce the same mosaic symptoms as in the suckers. Over time, systemic lignification occurs, producing a woody appearance on the main stem and branches. The prickles on the stem and branches become brittle and many on the leaves display signs of necrosis. Control plants inoculated with buffer only show no symptoms after 2 weeks. (FIG. 8)

TABLE 1

Analysis of Variance of the Effects of TSA Age Groups on the Day of First Symptom Appearance and Day of Death After Inoculation with TMGMV

| | First symptom | | | Death Day | | |
|---|---|---|---|---|---|---|
| Treatment | df | MS Means | F-value | df | MS Means | F-value |
| Trial 1 Age Groups | 5 | 49.95 | 152.97* | 5 | 136.37 | 44.7* |
| Trial 2 Age Groups | 5 | 49.27 | 284.0* | 5 | 640.91 | Infinity* |

Data for Trial 1 and Trial 2 were analyzed separately.
df = degrees of freedom
*$P < 0.0001$.

TABLE 2

Effect of Plant Age on First Symptom Appearance and First Death of Plants Inoculated with TMGMV ($P > 0.0001$)[a]

| First symptom appearance | | | Time to death | | |
|---|---|---|---|---|---|
| Plant Age[b] | N[c] | Mean[d] | Plant Age[b] | N[c] | Mean[d] |
| Trial 1 | | | | | |
| >12 | 6 | 10.0a | >12 | 6 | 21.5a |
| 7 | 10 | 9.4b | 7 | 10 | 18.0b |
| 3 | 10 | 5.0c | 3 | 10 | 13.0c |
| 2 | 10 | 5.0c | 2 | 10 | 13.0c |
| 1 | 9 | 5.0c | 1 | 9 | 13.0c |
| <1 | 10 | 4.8c | <1 | 10 | 10.0d |
| Trial 2 | | | | | |
| >12 | 5 | 6.7 | >12 | 5 | 25.0b |
| 7 | 10 | 11.6 | 7 | 10 | 30.0a |
| 3 | 10 | 6.0 | 3 | 10 | 12.0c |
| 2 | 10 | 6.0 | 2 | 10 | 12.0c |
| 1 | 10 | 6.0 | 1 | 10 | 12.0c |
| <1 | 10 | 6.0 | <1 | 10 | 10.0d |

[a]Means separated by Duncan's multiple range test.
[b]Plant age in months.
[c]N = number of replicates (TSA plants).
[d]Mean number of days to first symptoms or first plant death.

Effect of Temperature on TMGMV Disease Development

Since virus replication and disease development could be temperature-controlled, an experiment is conducted to determine the effect of temperature on TMGMV disease development in TSA. Three temperature regimes, continuous 18° C., continuous 32° C., and alternating 32/22° C., are established in controlled-environment plant growth chambers. All treatments have a 12-hour photoperiod with 250 $\mu E/m^2/s$ illumination provided by a combination of fluorescent and incandescent light bulbs. Plants of same ages are tested at each temperature regime. Plants in the 18° C. experiments are 5 and 7 months old for the first and second trials, respectively. Plants in the 32° C. experiment are 5 and 6 months old. For the 32/22° C. treatments, 3- to 4-month-old plants are used. The plants are manually inoculated with TMGMV and symptoms are recorded daily starting at 4 or 5 days after inoculation. The plants are kept in the chambers at the respective temperatures for 30 days after inoculation, except as stated below for plants at 32° C.

The temperature of the experiment has an impact on disease development (Table 3). TMGMV kills 100% of the inoculated TSA plants incubated at 18° C. and 32/22° C. in both trials. No symptoms develop at 32° C., possibly due to restriction of virus movement and/or multiplication at this temperature. At 18° C., the first symptoms appear in 7 and 9 days, respectively, in the first and second trials. At 32/22° C., the first symptoms appear in 7 and 10 days, respectively, in the two trials.

TABLE 3

Analysis of Variance of the Effect of Different Incubation Temperatures on First Symptom Appearance and Day of Death for Trials 1 and 2[a]

| | First symptom | | | First death | | |
|---|---|---|---|---|---|---|
| | df | MS Means | F-value | df | MS Means | F-value |
| Trial | 1 | 83.36 | 119.22* | 1 | 20.33 | 3.71 NS |
| Temp | 1 | 0.312 | 0.45 NS | I | 1282.67 | 234.18* |
| Trial* Temp | 1 | 10.03 | 14.35* | 1 | 86.11 | 15.72* |

[a]Three temperature regimes were tested: continuous 18° C., alternating temperatures of 32° C. (day) and 22° C. (night). The high temperature incubation trials were not included in the analysis due to lack of symptom development at 32° C. There were 8–10 plants per trial.
*P < 0.0001.
NS = not significant.

At 18° C. (low temperature), the TSA plants develop a high density of local lesions on the leaves. Fewer, scattered, local lesions develop 32/22° C. The local lesions appear on inoculated leaves as well as on noninoculated, newer leaves. Leaves with local lesions also develop severe chlorosis. The local lesions gradually coalesce and cover the entire leaf, but the stems remains mostly green with scattered necrotic spots. Plants die approximately 1 month after inoculation in both trials. The control plants remain healthy during both trials.

The asymptomatic plants from the 32° C. treatment are removed from this temperature after 17 days and placed in a greenhouse at 25±3° C. Five to 6 days after placement at 25±3° C., these plants develop systemic but nonlethal necrosis in 5 to 6 days. Several leaves absciss and others have wilted petioles and flaccid laminae. The older leaves gradually die and newly developing leaves express epinasty and mosaic similar to those seen on the suckers in the age-effect experiment. The new leaves are stunted and have necrotic flecks; even the prickles on the leaves are often necrotic. Over several weeks, the stems and branches gradually become lignified and develop a woody appearance throughout. Fruiting on these plants is limited or nonexistent and fruits that develop are destroyed by necrosis. Most plants die within 6–12 months after they are removed from 32° C. These results are consistent in the both trials.

The symptoms seen in TSA plants kept at 32° C. are typical of the attenuated symptom expression known in many plant-virus interactions. When three of these plants exhibiting this attenuated disease expression are reinoculated with TMGMV, they produce relatively more chlorosis and necrotic foliar lesions than seen at the time of inoculation, but do not die. This suggests the possibility that a milder TMGMV strain may have been selected at the high temperature and this milder strain may be cross-protecting the plant against the second, challenge-inoculation with the test isolate of TMGMV.

Reaction of Some Members of the Solanaceae to TMGMV

Reaction of some plants belonging to the Solanaceae family, to which TSA belongs, is studied to understand the range of nontarget plants that TMGMV might attack and the types of possible host reactions that might occur. Seeds of test plants are acquired from the Plant Introduction Station, Iowa State University, Ames, Iowa, except for tomato (*Lycopersicon esculentum* cv. Better Boy) plants that are obtained from Alachua Feed and Seed, Gainesville, Fla. Seeds are sown in Metro-Mix® 300 potting medium amended with Multicote®. One month after seedlings emerge, individual plants are transplanted into 6-cm pots containing Metro-Mix. The tomato seedlings are planted at this time. At inoculation, the plants are 1- to 3-month old after transplantation. Within each treatment, the plants are of the same age. The plants are manually inoculated as described previously and observed for symptoms. There are four plants in each inoculated treatment and two in the controls. The experiment is performed two times.

A reliable test to detect viral infections and identify the virus present is the indirect enzyme-linked immunosorbant assay (ELISA). This assay is used to confirm the presence and identity of TMGMV infections in inoculated plants. For ELISA, newly developed leaves from both inoculated and healthy controls are collected 2 to 3 weeks after inoculation and ca. 5 g of the leaf tissue are crushed in a mechanical sap extractor and diluted to a 1:1 volume with sterile deionized water. This crude sap sample is diluted 1:10 with an extraction. buffer ($Na_2SO_3$, polyvinylpyrrolidone-40, bovine serum albumin, phosphate buffered saline, and 0.05% Tween-20 [PBST], pH96). TMGMV antisera are diluted 1:1000 in PBST at pH 7.4. Whole-molecule goat anti-rabbit alkaline phosphatase conjugate purchased from Sigma Chemical Co. (St. Louis, Mo.) is diluted 1:20,000 and reacted with the TMGMV-TSA-buffer extract. The absorbance values of the reaction mixture are recorded at (405 nm) at 15-minute intervals with a spectrophotometer. A sample is considered positive if the average of three reaction wells per sample is greater or equal to three times the value of healthy control value. A positive ELISA reading indicates the presence of the virus in the inoculated plants, irrespective of the expression of visible symptoms.

Among the members of the Solanaceae family screened, some Solanum species and *Capsicum annuum* cultivars are susceptible to TMGMV. (Table 4). Approximately one-third of the species tested are susceptible, but each reacts differently to TMGMV. Eighty percent of the susceptible species produce a hypersensitive response (HR).

TABLE 4

Reaction of Some Solanum Species to TMGMV

| | Absorbance values (405 nm)[a] | | Host |
|---|---|---|---|
| Host species | Treated | Control | Reaction[b] |
| *C. annuum* L. (Jalapeño) | 1.09 | 0.303 | SHR+ |
| *C. annuum* cv. California Wonder | | | SHR+ |
| *L. esculentum* Mill. cv. Better Boy | | | |
| *S. acerifolium* Dunal | 0.398 | 0.277 | |
| *S. aculeatissimum* Jacq. | 0.186 | 0.18 | |
| *S. aethiopicum* L. | 0.08 | 0.09 | |
| *S. americanum* Mill. | 0.02 | 0.07 | LHR |
| *S. anguivi* Lam. | 0.02 | 0.03 | LHR |
| *S. atropurpureum* Schrank | | | |
| *S. aviculare* G. Forst. | | | |
| *S. capsicoides* All. | | | |
| *S. caripense* Dunal | | | |
| *S. ciliatum* Lam. | | | |
| *S. elaeagnifolium* Cav. | 0.02 | 0.03 | |
| *S. ferox* auct. = *S. lasiocarpum* Dunal | | | |
| *S. gilo* Raddi = *S. aethiopicum* L. | | | LHR |
| *S. incanum* L. | | | |
| *S. linnaeanum* Hepper & P.M.L. Jaeger | | | |
| *S. macrocarpon* L. | | | M+ |
| *S. mammosum* L. | | | |
| *S. melongena* L. | | | |
| *S. nigrum* L. var. villosum L. = *S. villosum* Mill. | 0.44 | 0.06 | +NS |

TABLE 4-continued

Reaction of Some Solanum Species to TMGMV

| Host species | Absorbance values (405 nm)[a] Treated | Control | Host Reaction[b] |
|---|---|---|---|
| *S. nodiflorum* Jacq. = *S. americanum* Mill. | 0.14 | 0.09 | LHR |
| *S. pseudocapsicum* L. | 0.015 | 0.02 | LHR |
| *S. rostratum* Dunal | 0.19 | 0.03 | +NS |
| *S. sessiliflorum* Dunal | | | LHR |
| *S. sisymbriifolium* Lam. | 0.05 | 0.03 | |
| *S. spinosissium* Lodd. ex G. Don, nom. nud. | 0.2 | 0.01 | M+ |
| *S. stramoniifolium* Jacq. | 0.06 | 0.04 | |
| *S. suaveolens* Kunth & C.P. Bouche | 0.64 | 0.47 | |
| *S. tampicense* Dunal | | | |

[a]Samples screened by indirect ELSIA. Virus-free control plants in each treatment remained asymptomatic and healthy.
[b]Host reactions: + = positive reading by ELISA, blank space = negative reading. LHR = localized hypersensitive response, SHR = systemic hypersensitive response, M = mosaic symptoms, NS = no symptoms.

*Solanum americanum, S. anguivi, S. gilo, S. nodifolium, S. pseudocapsicum,* and *S. sessilifolium* produces localized HR. The presence of TMGMV infection is detected by indirect ELISA in *S. macrocarpon, S. nigrum, S. rostratum,* and *S. spinosissimum.* Of these, *S. nigrum* and *S. rostratum* do not develop visible symptoms, while *S. macrocarpon* and *S. spinosissimum* develop mosaic symptoms. The cultivated pepper species *Capsicum annuum* (California Wonder and Jalapeño) develops systemic HR. In the first trial, two California Wonder (bell pepper) plants were killed within 2 to 3 weeks after inoculation. In the second trial, one jalapeño pepper plant was killed. The remaining *C. annuum* plants have necrotic lesions on leaves and stems, minor leaf distortion, fruit malformation, and stunting. *Lycopersion esculentum* cv. Better Boy, (tomato) and *Solanum melongena* (eggplant), as. well as the remaining Solanum species, are immune and therefore nonhosts to TMGMV. This is confirmed by the indirect ELISA absorbance values for leaf extracts (antigen samples) from corresponding inoculated and control plants (Table 4).

Field Trials of Efficacy of TMGMV as a Herbicide for TSA

The efficacy of TMGMV as a bioherbicide for TSA is established through field trials. Trials are conducted at two sites. Field Site No. 1 is in a 5-ha cattle pasture near Hawthorne, Fla., which has a moderate density of TSA infestation. The TSA plants in this field range in maturities from small seedlings to large-canopied, fruit-bearing plants. The trial is performed two times at this site.

Effects of two application methods and two inoculum levels are compared in trail 1. The application methods consist of hand inoculation and pressure-infiltration, for example, with the aid of a $CO_2$-propelled backpack sprayer. The sprayer is set at pressure between 20 and 100 psi, preferably 60 psi and has a Teejet 5500 nozzle. To insure infection, the nozzle is pressed against the adaxial surface of the TSA leaves, while spraying. After infiltration, the inoculated spots are inspected for signs of water soaking. The inoculum levels consist of 0.5 or 1.0 gram of TMGMV-infected Turkish Samsun nn tissue extracted in one liter of buffer for the pressure-infiltrated treatments in trial 1 and 1.5 and 2.0 g in trial 2. Hand-inoculated treatment is done as described previously by rubbing the inoculum on the abaxial leaf surface. Five to eight leaves per plant are inoculated by each inoculation method. There are 30 plants per treatment. Each plant is measured for plant height and canopy diameter. Canopy size is determined by taking the average of two measurements (the longest width and the width perpendicular to the longest width).

The inoculum is prepared by triturating up to 10.0 g vacuum-dried, TMGMV-infected Turkish Samsun nn tobacco leaf tissue (preferably 0.5, 1.0, 1.5, and 3.0 g) in 10–20 ml of sodium phosphate buffer (pH 7.2). The extracted samples are then filtered by means known in the art, for example, strained through sterile cheesecloth into capped vials. At the time of inoculation, the virus-buffer mixture is poured into 1 liter of sterile deionized water. One gram of carborundum (320 grit) was added to each liter to serve as an abrasive. To prevent contamination of the controls, the virus-free control treatments are applied first followed by the virus treatments.

After 5 days, the plants are rated for symptom appearance and then rated at 2- to 3-day intervals. The data are analyzed using the SAS program (Statistical Analysis System, Cary, N.C.) by analysis of variance. Significant means are separated by Duncan's multiple range test and Tukey's Honest Significant Difference test.

Two additional field trials (Field Site Nos. 2 and 3) are conducted at the Deseret Cattle and Citrus Company, St. Cloud, Fla. Field Site No. 2 is located in a pasture, under a cypress hammock and contains 100 plants each for the inoculated and control treatments. Field Site No. 3 is located in an open pasture and contains 70 plants each for the inoculated and control treatments. The plants are randomly assigned treatments and identified with colored flags or plastic labels. The inoculum is prepared in the same manner as the trials at Field Site No. 1, but consists of 1.5 g of TMGMV-infected leaf tissue per liter concentration. Only the pressure-infiltration method is used to inoculate the plants at Field Site No. 2. Data are recorded at 14, 25, and 51 days after inoculation and analyzed using the SAS program.

At Field Site No. 1, TSA plants of various sizes and maturities are killed following inoculation with TMGMV. (Table 5). The method of inoculation or inoculum concentration does not affect disease development or plant kill. Both the hand-inoculation and pressure-infiltration methods are equally effective. (Table 6). In addition, the inoculum concentrations of 0.5, 1.0, 1.5, and 3.0 g/liter are equally effective. The canopy diameters of plants inoculated in trials 1 and 2 range from 0.5–2.0 m and plant height ranged from 18–110 cm. A regression analysis indicates no correlation between plant size and first appearance of systoms or first mortality.

TABLE 5

Analysis of Variance of the Effect of TMGMV Inoculation on Day of First Symptom Expression and Day of First Death in Field Trials 1 and 2 ($P > 0.0001$) at Field Site No. 1.

| Trial 1 First symptom | | | Trial 2 First symptom | | |
|---|---|---|---|---|---|
| df | MS Means | F-value | df | MS Means | F-value |
| 3 | 7.34 | 881 | 3 | 7.26 | 450.68 |
| Days until death | | | Days until death | | |
| df | MS Means | F-value | df | MS Means | F-value |
| 3 | 5.65 | 72.89 | 3 | 5.99 | 90.17 |

TABLE 6

Effects of TMGMV inoculation on TSA Plants in Field Trials 1 and 2 (P > 0.0001) at Field Site No. 1.

| Percentage of TSA plants expressing symptoms | | | | | |
|---|---|---|---|---|---|
| Field trial 1[a] | | | Field trial 2[b] | | |
| % Inoculated plants | N[c] | Treatment[d] | % Inoculated plants | N | Treatment |
| 100.0 a | 30 | 0.5 g/liter infilt. | 100.0 a | 32 | 1.5 g/liter infilt. |
| 100.0 a | 30 | Hand inoc. | 97.0 a | 32 | 3.0 g/liter inilt. |
| 97.0 a | 30 | 1 g/liter infilt. | 97.0 a | 30 | Hand inoc. |
| 0.0 b | 30 | Control | 0.00 b | 30 | Control |

| Percentage of mortality of TSA plants | | | | | |
|---|---|---|---|---|---|
| % inoculated plants | N | Treatment | % inoculated plants | N | Treatment |
| 93.0 a | 30 | 0.5 g/liter infilt. | 97.0 a | 32 | 1.5 g/liter infilt. |
| 90.0 a | 30 | Hand inoc. | 83.0 a | 32 | Hand inoc. |
| 87.0 a | 30 | 1 g/liter infilt. | 94.0 a | 30 | 3.0 g/liter infilt. |
| 0.0 b | 30 | Control | 0.0 b | 30 | Control |

[a]Based on Tukey's HSD test.
[b]Based on Duncan's multiple range test.
[c]Number of plants per treatment.
[d]Amount of inoculum and application method: infilt. = plants inoculated by pressure-infiltration of inoculum on the adaxial leaf surface. Hand inoc. = Inoculum applied to abaxial leaf surface by hand-rubbing with inoculum containing leaf extract; the precise amount of inoculum is not characterized.
Control = control plants mock-inoculated with buffer only.

Figure 9A:
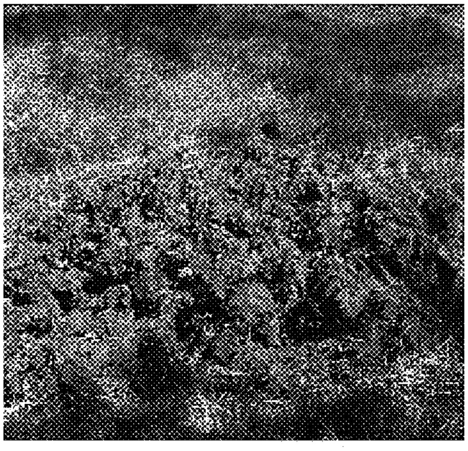
FIG. 9A is a photograph depicting manually inoculated plants prior to symptom expression.
Figure 9B:
FIG. 9B is a photograph depicting the manually inoculated plants of FIG. 9A, two-three weeks post inoculation.
Figure 10:
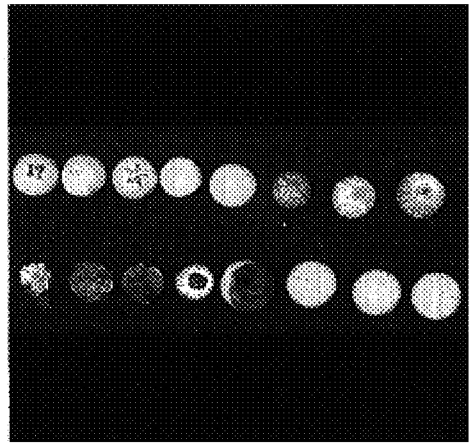
FIG. 10 is a photograph depicting the effects of TMGMV on TSA fruits. Top row shows fruits from control plants; bottom row shows fruits from inoculated plants.

Referring now to FIGS. 9A and 9B, the first symptoms on inoculated plants in the field are foliar lesions, followed by systemic necrosis. No suckers appear during the 2-month period when the data are collected. Many fruits, still maturing at the time of inoculation, exhibit necrotic symptoms, and most of the necrotic fruits are shriveled and withered. (FIG. 10). Fruits that are mature at the time of inoculation remain healthy even though the plant has necrosed. Healthy, mature fruits collected from two surviving plants have highly viable seeds. The mock-inoculated control plants remain healthy.

The efficacy of TMGMV as a biological control agent is confirmed also in the Deseret Ranch field trials (Table 7). At Field Site No. 2, disruptions from cattle congregating under the hammock and flooding due to heavy rainfall prevent data collection at this site beyond 14 days after inoculation. On day 14, the remaining plants, 47 inoculated TSA plants and 35 control plants, are rated. Of the inoculated plants, 59.5% are killed by TMGMV by this day compared with 5.7% mortality among the control plants. The remaining inoculated plants have foliar lesions and signs of necrosis.

TABLE 7

| | | Days after inoculation | | |
|---|---|---|---|---|
| Trial Sites[a] | Treatment | 14 | 25 | 51 |
| Field Site No. 2 | Inoculated | 59.5 A[b] | NA | NA |
| | Control | 5.7 B | NA | NA |

TABLE 7-continued

| | | Days after inoculation | | |
|---|---|---|---|---|
| Trial Sites[a] | Treatment | 14 | 25 | 51 |
| Field Site No. 3 | Inoculated | 3.0 A | 75.0 A | 88.4 A |
| | Control | 0.0 A | 1.6 B | 1.6 B |

Percentage of TSA Plants Killed by TMGMV at Field Site Nos. 2 and 3.
[a]At Field Site No. 2, the trial is abandoned after 14 days due to disruption of the site by cattle and flooding. The data are from 47 inoculated and 35 control plants. Field Site No. 3 has 70 plants per treatment.
[b]Within a column, numbers followed by different letters are significantly different at P = 0.01 using Duncan's multiple range test.

At Field Site No. 3, by 25 days, 75% of the inoculated TSA plants and 1.6% of the control plants are killed. No suckers emerge from either th treated or the control plants. By day 51, 88.4% of the inoculated plants have died compared to 1.6% of the control plants. The control plants probably die due to cross-contamination by TMGMV or from other biotic or abiotic causes.

Mechanism of Systemic Hypersensitive Killing of TSA

Hypersensitive response (HR) can be described as a race between the speed of virus replication and movement within the plant, and the speed of plant defense response in confining the virus. Plant death, as seen in TSA inoculated with TMGMV, is the manifestation of the virus having won the race. The hypersensitive response is an active response in which the plant recognizes the pathogen and responds defensively in an attempt to confine the pathogen to the initial infection area. The hypersensitive response normally results in localized cell death. Complete or near complete death of the whole plant, as is seen in the TSA-TMGMV system, is rare. Based on the recent isolation and description of HR-type resistance genes, the R genes, and pathogen avirulence genes, avr genes in other plant pathogen systems, the trigger of the hypersensitive response is a specific interaction between a receptor domain of the R gene product and a specific pathogen elicitor, a product of the avirulence gene. Different forms of the elicitor can interact differently with the resistance gene. Strong elicitors induce the resistance response quickly, with the pathogen then being confined to a small area surrounding the initial infection site. Weak elicitors slowly induce the hypersensitive response, allowing the pathogen to spread further before it is confined, if at all. These differences are probably due to the availability or affinity of the elicitor to the receptor. Thus, viral elicitors appear to be any viral product that the plant can recognize in order to mobilize a resistance response (Dawson, 1999; Chisholm et al., 2000). Different plants recognize the same viral gene product in a different manner. Conversely, viruses evolve by generating viral gene products that escape host recognition and thus avoid the hypersensitive response that limits their ability to systemically infect the host (Dawson, 1999).

All tobamoviral gene products have been shown to act as an elicitor in some plant. The tobamovirus coat protein was the first viral gene product recognized as an elicitor of an hypersensitive response in tobacco containing the N' gene, (Saito et al., 1987). The movement protein gene product has been mapped as the elicitor of the hypersensitive response in tomato containing TM-2 and TM-$2^2$ genes, (Weber and Pfitzner, 1998). N-gene-mediated hypersensitive response in tobacco is induced by the tobamovirus replicase. (Padgett et al., 1997).

Several techniques have proven highly effective in identifying viral factors responsible for elicitation of the hypersensitive response. The first is the production of chimeric viruses consisting of genomic segments from different viruses. This method is particularly useful in systems with closely related viruses that have distinct host resistance phenotypes. In many systems, however, both resistance inducing and/or noninducing viruses do not exist. To overcome this problem, researchers are utilizing heterologous viral vectors for the expression of specific viral components in attempts to assign avirulence functions (Culver, 1997; Shivprasad et al., 1999).

The induction of the hypersensitive response in plants does not necessarily require the presence of the pathogen responsible for the elicitor. Culver and Dawson (1991) showed that TMV coat protein expression alone in transgenic tobacco containing the N' gene produced the hypersensitive phenotype. Erickson et al. (1999) showed that helicase domain of the TMV replicase proteins induces N-mediated defense response in tobacco in the absence of virus replication. Also, Duan et al. (1999), using a transient expression system demonstrated that a single, host-specific bacterial pathogenicity gene elicited, in the absence of the pathogen, host-specific symptoms diagnostic of the disease caused by the bacterial pathogen. The ability of an elicitor to induce the hypersensitive response in certain plants would eliminate the need to utilize the intact virus. Therefore, the TMGMV elicitor alone can be used as an herbicide.

Inasmuch as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

REFERENCES

Akanda, R. U., Dowler, C. C., Mullahey, J. J., and Shilling, D. G. 1997. Influence of postemergence herbicides on tropical soda apple (*Solanum viarum*) and Bahiagrass (*Paspalum notatum*). Weed Technol. 11:656–661.

Chisholm, S. T., Mahajan, S. J., Whitham, S. A., Yamamoto, M. L. and Carrington, J. C. 2000. Cloning of the Arabidopsis RTM1 gene, which controls restriction of long-distance movement of tobacco etch virus. Proc. Natl. Acad. Sci. 97: 489–494.

Culver, J. N. 1997. Viral avirulence genes. Chapter 6. Pages 196–219 in: G. Stacey and N. T. Keen, eds. Plant-Microbe Interactions, Vol. 2. Chapman & Hall, New York.

Culver, J. N., and Dawson, W. O. 1991. Tobacco mosaic virus elicitor coat protein genes produce a hypersensitive phenotype in transgenic Nicotiana sylvestris plants. Mol. Plant-Microbe Interact. 4:458–463.

Dawson, W. O. 1999. Tobacco mosaic virus virulence and avirulence. Phil. Trans. R. Soc. Lond. B 354:643–651.

Duan, Y. P., Castañeda, A., Zhao, G., Erdos, G., Gabriel, D. W. 1999. Expression of a single, host specific, bacterial pathogenicity gene in plant cells elicits division, enlargement, and cell death. Molec. Plant-Microbe Interact. 12:556–560.

Erickson, F. L., Holzberg, S., Calderon-Urrea, A., Handley, V., Axtell, M., Corr, C., and Baker, B. 1999. The helicase domain of the TMV replicase proteins induces the N-mediated defense response in tobacco. Plant Journal 18, 67–75.

McGovern, R. J., Polston, J. E., and Mullahey, J. J. 1994. *Solanum viarum* Dunal: weed reservoir of plant viruses in Florida. Int. J. Pest Manage. 40:270–273.

Mullahey J. J. 1996. Tropical soda apple (*Solanum viarum* Dunal), a biological pollutant threatening Florida. Castanea 61:255–260.

Padgett, H. S. Watanabe, Y., arid Beachy, R. N. 1997. Identification of the TMV replicase sequence that activates the N gene-mediated hypersensitive response. Mol. Plant-Microbe Interact. 10:709–715.

Purcifull, D. E. 1990. Ouchterlony double-diffusion tests in the presence of sodium dodecyl sulfate for detection of virion proteins and virus-induced inclusion proteins. Pages 179–196 in: R. Hampton, E. Ball, and S. De Boer, eds., Serological Methods for the Detection and Identification of Viral and Bacterial Plant Pathogens, APS Press, St. Paul, Minn.

Saito, T., Meshi, T., Takamatsu, N., and Okado, Y. 1987. Coat protein gene sequences of tobacco mosaic virus encodes host response determinant. Proc. Natl. Acad. Sci. USA 85:6074–6077.

Shivprasad, S., Pogue, G. P., Lewandowski, J., Hidalgo, J., Donson, J., Grill, L. K., and Dawson, W. O. 1999. Heterologous sequences greatly affect foreign gene expression in tobacco mosaic virus-based vectors. Virology 255:312–323.

Weber, H. and Pfitzner, J. P. 1998. Tm-$2^2$ resistance in tomato requires recognition of the carboxy terminus of the movement protein of tomato mosaic virus. Molec. Plant-Microbe Interact. 11:498–503.

What is claimed is:

1. A method of inducing lethal hypersensitive response in tropical soda apple plants comprising the steps of:

(a) obtaining an inoculation solution comprising Tobacco Mild Green Mosaic Virus, buffer and water; said obtaining step comprising extracting said virus from vacuum-dried host plant tissue by trituration; and (b) applying said inoculation solution to the adaxial surface of the leaves of said tropical soda plant by sprayer application.

2. The method of claim 1 wherein said buffer is sodium phosphate.

3. The method of claim 1 wherein said sprayer application is performed by a sprayer.

4. The method of claim 3 wherein said sprayer is set for application at a pressure of between 20 and 100 p.s.i.

5. The method of claim 3 wherein said sprayer is set at a pressure of about 60 p.s.i.

6. A method of inducing lethal hypersensitive response in tropical soda apple plants comprising the steps of:

(a) extracting Tobacco Mild Green Mosaic Virus from vacuum-dried host plant tissue, by triturating said host plant tissue in a buffer, wherein the ratio of said host plant tissue to said buffer is up to 1 g/ml;

(b) filtering extracted virus sample through a filter;

(c) preparing an inoculation solution by diluting the extracted sample with water;

(d) applying said inoculation solution to the adaxial surface of the leaves of said tropical soda apple plant.

7. The method of claim 6 wherein said buffer is sodium phosphate.

8. The method of claim 6 wherein said application is performed by sprayer.

9. The method in claim 8 wherein said sprayer is set at pressure between 20 and 100 p.s.i.

10. The method of claim 8 or 9 wherein said sprayer is set at a pressure of about 60 p.s.i.

* * * * *

UNITED STATES PATENT AND TRADEMARK OFFICE

CERTIFICATE OF CORRECTION

PATENT NO. : 6,689,718 B2 
DATED : February 10, 2004
INVENTOR(S) : Raghavan Charudattan, Matthew Scott Pettersen and Ernest Hiebert It is certified that error appears in the above-identified patent and that said Letters Patent is hereby corrected as shown below:

Column 3,
Line 33, "Immokalee, Fla." should read -- Immokalee, Florida. --

Column 8,
Line 1, "Gainesville, Fla." should read -- Gainesville, Florida. --
Lines 20-21, "...extraction. buffer…" should read -- ...extraction buffer…--

Column 9,
Line 38, "...as. well as…" should read -- ...as well as… --

Signed and Sealed this

Sixth Day of July, 2004

JON W. DUDAS
*Acting Director of the United States Patent and Trademark Office*